(12) United States Patent
Crawford et al.

(10) Patent No.: US 8,277,408 B2
(45) Date of Patent: *Oct. 2, 2012

(54) SAFETY NEEDLE ASSEMBLY

(75) Inventors: Jamieson William Maclean Crawford, Cliffside Park, NJ (US); Michael Bennett, Summit, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1507 days.

This patent is subject to a terminal disclaimer.

(21) Appl. No.: 10/612,591

(22) Filed: Jul. 1, 2003

(65) Prior Publication Data

US 2004/0059302 A1    Mar. 25, 2004

Related U.S. Application Data

(63) Continuation of application No. 10/173,239, filed on Jun. 14, 2002, now Pat. No. 6,648,855.

(51) Int. Cl.
*A61M 5/32* (2006.01)
*A61M 5/00* (2006.01)

(52) U.S. Cl. ......... 604/110; 604/192; 604/263; 128/919

(58) Field of Classification Search .............. 604/110, 604/164.01, 164.08, 187, 192, 197–198, 604/263; 128/919
See application file for complete search history.

(56) References Cited

U.S. PATENT DOCUMENTS

| | | | |
|---|---|---|---|
| 1,779,451 A | 10/1930 | Sponsel | |
| 2,004,050 A | 6/1935 | Kerk | |
| 2,700,385 A | 1/1955 | Ortiz | |
| 2,836,942 A | 6/1958 | Miskel | |
| 2,854,976 A | 10/1958 | Heydrich | |
| 2,953,243 A | 9/1960 | Roehr | |
| 3,021,942 A | 2/1962 | Hamilton | |
| 3,073,307 A | 1/1963 | Stevens | |
| 3,074,542 A | 1/1963 | Myerson et al. | |
| 3,255,873 A | 6/1966 | Speelman | |
| 3,294,231 A | 12/1966 | Vanderbeck | |
| 3,323,523 A | 6/1967 | Scislowicz et al. | |
| 3,329,146 A | 7/1967 | Waldman, Jr. | |
| 3,333,682 A | 8/1967 | Burke | |
| 3,367,488 A | 2/1968 | Hamilton | |
| 3,485,239 A | 12/1969 | Vanderbeck | |
| 3,537,452 A | 11/1970 | Wilks | |
| 3,610,240 A | 10/1971 | Harautuneian | |
| 3,658,061 A | 4/1972 | Hall | |
| 3,828,775 A | 8/1974 | Armel | |
| 3,890,971 A | 6/1975 | Leeson et al. | |
| 3,904,033 A | 9/1975 | Haerr | |
| 3,934,722 A | 1/1976 | Goldberg | |

(Continued)

FOREIGN PATENT DOCUMENTS

GB    1 233 302    5/1971

(Continued)

*Primary Examiner* — Matthew F Desanto
(74) *Attorney, Agent, or Firm* — The Webb Law Firm

(57) ABSTRACT

The present invention is a safety shield assembly having a shield and a collar for connecting the shield to a fluid handling device whereby the shield may be pivoted with respect to the collar. Preferably, the safety shield assembly may be used with a needle assembly, an intravenous infusion set a syringe, a catheter or other fluid handling devices or assemblies that contain piercing elements. The shield includes a cannula channel with a finger lock for preventing re-exposure of the used needle.

22 Claims, 19 Drawing Sheets

U.S. PATENT DOCUMENTS

| | | | |
|---|---|---|---|
| 3,968,876 | A | 7/1976 | Brookfield |
| 4,113,090 | A | 9/1978 | Carstens |
| 4,139,009 | A | 2/1979 | Alvarez |
| 4,175,008 | A | 11/1979 | White |
| 4,300,678 | A | 11/1981 | Gyure et al. |
| RE31,086 | E | 11/1982 | Johnson, Jr. et al. |
| 4,375,849 | A | 3/1983 | Hanifl |
| 4,430,082 | A | 2/1984 | Schwabacher |
| 4,592,744 | A | 6/1986 | Jagger et al. |
| 4,634,428 | A | 1/1987 | Cuu |
| 4,643,722 | A | 2/1987 | Smith, Jr. |
| 4,659,330 | A | 4/1987 | Nelson et al. |
| 4,664,249 | A | 5/1987 | Gherardi |
| 4,664,259 | A | 5/1987 | Landis |
| 4,664,654 | A | 5/1987 | Strauss |
| 4,671,408 | A | 6/1987 | Raines et al. |
| 4,681,567 | A | 7/1987 | Masters et al. |
| 4,695,274 | A | 9/1987 | Fox |
| 4,702,738 | A | 10/1987 | Spencer |
| 4,723,943 | A | 2/1988 | Spencer |
| 4,728,320 | A | 3/1988 | Chen |
| 4,728,321 | A | 3/1988 | Chen |
| 4,731,059 | A | 3/1988 | Wanderer et al. |
| 4,735,311 | A | 4/1988 | Lowe et al. |
| 4,735,618 | A | 4/1988 | Hagen |
| 4,737,144 | A | 4/1988 | Choksi |
| 4,738,663 | A | 4/1988 | Bogan |
| 4,743,233 | A | 5/1988 | Schneider |
| 4,746,008 | A | 5/1988 | Heverly et al. |
| 4,747,836 | A | 5/1988 | Luther |
| 4,747,837 | A | 5/1988 | Hauck |
| 4,772,272 | A | 9/1988 | McFarland |
| 4,778,453 | A | 10/1988 | Lopez |
| 4,781,697 | A | 11/1988 | Slaughter |
| 4,782,841 | A | 11/1988 | Lopez |
| 4,790,828 | A | 12/1988 | Dombrowski et al. |
| 4,793,484 | A | 12/1988 | Schoettle |
| 4,795,432 | A | 1/1989 | Karczmer |
| 4,795,443 | A | 1/1989 | Permenter et al. |
| 4,801,295 | A | 1/1989 | Spencer |
| 4,804,372 | A | 2/1989 | Laico et al. |
| 4,813,426 | A | 3/1989 | Haber et al. |
| 4,816,022 | A | 3/1989 | Poncy |
| 4,816,024 | A | 3/1989 | Sitar et al. |
| 4,819,659 | A | 4/1989 | Sitar |
| 4,820,277 | A | 4/1989 | Norelli |
| 4,826,490 | A | 5/1989 | Byrne et al. |
| 4,826,491 | A | 5/1989 | Schramm |
| 4,838,871 | A | 6/1989 | Luther |
| 4,842,587 | A | 6/1989 | Poncy |
| 4,846,796 | A | 7/1989 | Carrell et al. |
| 4,850,968 | A | 7/1989 | Romano |
| 4,850,976 | A | 7/1989 | Heinrich et al. |
| 4,850,977 | A | 7/1989 | Bayless |
| 4,850,978 | A | 7/1989 | Dudar et al. |
| 4,850,994 | A | 7/1989 | Zerbst et al. |
| 4,850,996 | A | 7/1989 | Cree |
| 4,858,607 | A | 8/1989 | Jordan et al. |
| 4,863,434 | A | 9/1989 | Bayless |
| 4,863,435 | A | 9/1989 | Sturman et al. |
| 4,863,436 | A | 9/1989 | Glick |
| 4,867,746 | A | 9/1989 | Dufresne |
| 4,872,552 | A | 10/1989 | Unger |
| 4,874,383 | A | 10/1989 | McNaughton |
| 4,874,384 | A | 10/1989 | Nunez |
| 4,883,469 | A | 11/1989 | Glazier |
| 4,886,503 | A | 12/1989 | Miller |
| 4,888,001 | A | 12/1989 | Schoenberg |
| 4,892,107 | A | 1/1990 | Haber |
| 4,892,521 | A | 1/1990 | Laico et al. |
| 4,900,309 | A | 2/1990 | Netherton et al. |
| 4,909,791 | A | 3/1990 | Norelli |
| 4,909,792 | A | 3/1990 | Norelli |
| 4,921,096 | A | 5/1990 | McFarlane |
| 4,927,018 | A | 5/1990 | Yang et al. |
| 4,944,397 | A | 7/1990 | Miller |
| 4,966,591 | A | 10/1990 | Yuen |
| 4,976,699 | A | 12/1990 | Gold |
| 4,982,842 | A | 1/1991 | Hollister |
| 5,011,475 | A | 4/1991 | Olson |
| 5,011,479 | A | 4/1991 | Le et al. |
| 5,055,102 | A | 10/1991 | Sitnik |
| 5,078,693 | A | 1/1992 | Shine |
| 5,116,325 | A | 5/1992 | Paterson |
| 5,135,509 | A | 8/1992 | Olliffe |
| 5,139,489 | A | 8/1992 | Hollister |
| 5,151,089 | A | 9/1992 | Kirk, III et al. |
| 5,154,285 | A | 10/1992 | Hollister |
| 5,188,611 | A | 2/1993 | Orgain |
| 5,197,954 | A | 3/1993 | Cameron |
| 5,207,653 | A | 5/1993 | Janjua et al. |
| 5,232,454 | A | 8/1993 | Hollister |
| 5,232,455 | A | 8/1993 | Hollister |
| 5,242,417 | A | 9/1993 | Paudler |
| 5,277,311 | A | 1/1994 | Hollister |
| 5,312,369 | A | 5/1994 | Arcusin et al. |
| 5,401,251 | A | 3/1995 | Hui |
| 5,405,332 | A | 4/1995 | Opalek |
| 5,423,765 | A | 6/1995 | Hollister |
| 5,462,534 | A | 10/1995 | Debreczeni |
| 5,485,854 | A | 1/1996 | Hollister |
| 5,486,163 | A | 1/1996 | Haynes |
| 5,490,841 | A | 2/1996 | Landis |
| 5,509,907 | A * | 4/1996 | Bevilacqua ............... 604/263 |
| 5,533,984 | A | 7/1996 | Parmigiani |
| 5,584,816 | A | 12/1996 | Gyure et al. |
| 5,599,313 | A | 2/1997 | Gyure et al. |
| 5,599,318 | A | 2/1997 | Sweeney et al. |
| 5,603,699 | A | 2/1997 | Shine |
| 5,632,732 | A * | 5/1997 | Szabo et al. ............. 604/192 |
| 5,643,219 | A | 7/1997 | Burns |
| 5,662,617 | A | 9/1997 | Odell et al. |
| 5,665,075 | A * | 9/1997 | Gyure et al. ............. 604/263 |
| 5,669,889 | A | 9/1997 | Gyure et al. |
| 5,693,022 | A | 12/1997 | Haynes |
| 5,702,369 | A | 12/1997 | Mercereau |
| 5,733,265 | A | 3/1998 | Bachman et al. |
| 5,807,351 | A | 9/1998 | Kashmer |
| 5,836,920 | A | 11/1998 | Robertson |
| 5,885,249 | A | 3/1999 | Irisawa |
| 5,913,846 | A | 6/1999 | Szabo |
| 5,993,426 | A | 11/1999 | Hollister |
| 6,077,253 | A | 6/2000 | Cosme |
| 6,080,137 | A | 6/2000 | Pike |
| 6,120,482 | A | 9/2000 | Szabo |
| 6,139,533 | A | 10/2000 | Xia et al. |
| RE37,100 | E | 3/2001 | Hollister |
| RE37,252 | E | 7/2001 | Hollister |
| 6,319,232 | B1 | 11/2001 | Kashmer |
| 6,328,713 | B1 | 12/2001 | Hollister |
| 6,334,857 | B1 | 1/2002 | Hollister et al. |
| 6,648,855 | B2 * | 11/2003 | Crawford et al. ............. 604/110 |
| 6,699,217 | B2 * | 3/2004 | Bennett et al. ............... 604/110 |
| 7,128,726 | B2 * | 10/2006 | Crawford et al. ............. 604/110 |
| 7,220,249 | B2 * | 5/2007 | Hwang et al. ............... 604/263 |

FOREIGN PATENT DOCUMENTS

| | | |
|---|---|---|
| GB | 2 239 604 | 7/1991 |
| GB | 2 239 607 | 7/1991 |
| GB | 2 240 273 | 7/1991 |
| GB | 2 240 477 | 8/1991 |
| WO | WO 87/07162 | 12/1987 |
| WO | WO 90/01348 | 2/1990 |
| WO | WO 91/09637 | 7/1991 |
| WO | WO 91/09638 | 7/1991 |
| WO | WO 91/09639 | 7/1991 |
| WO | WO 93/16745 | 9/1993 |

* cited by examiner

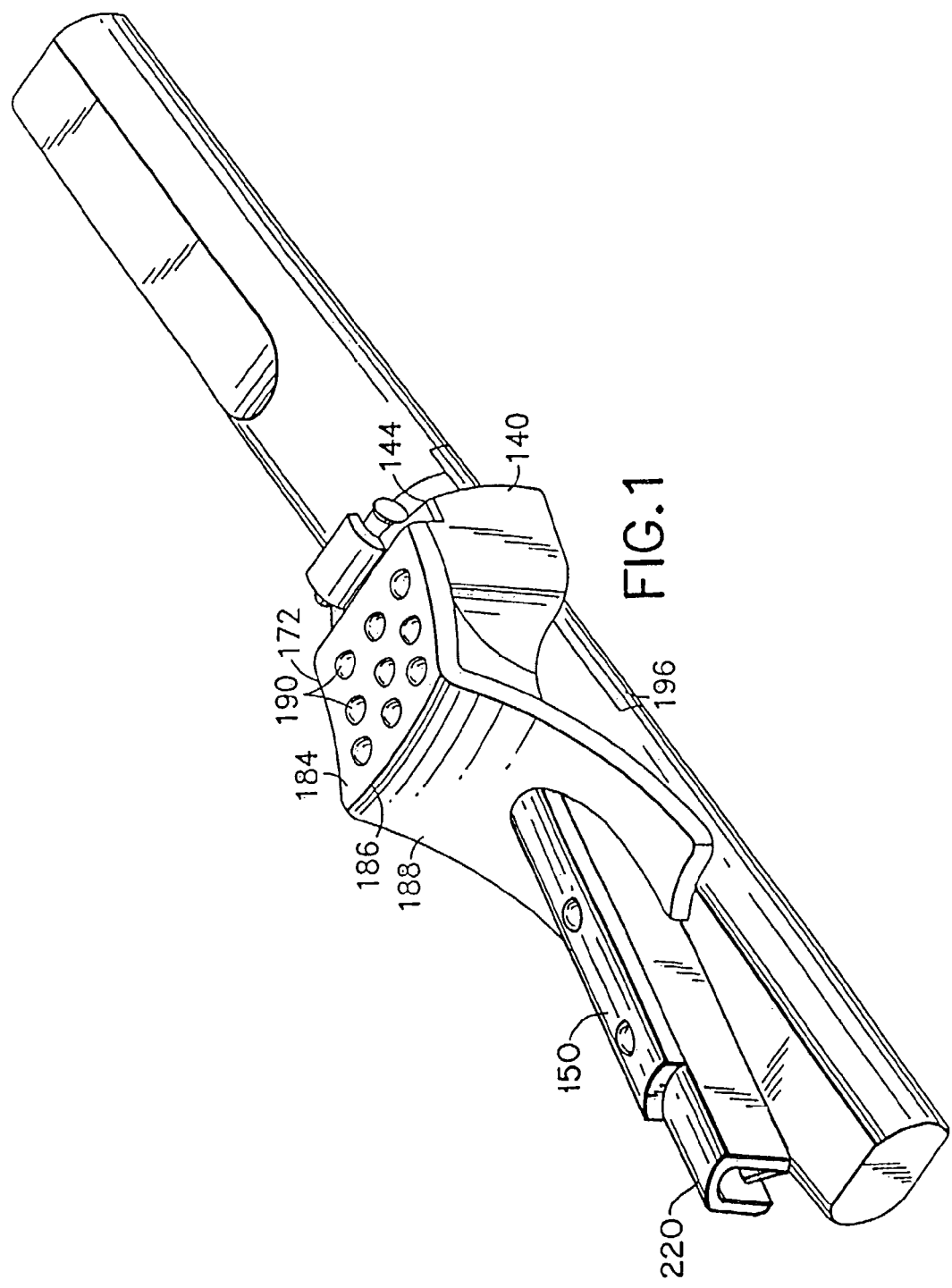

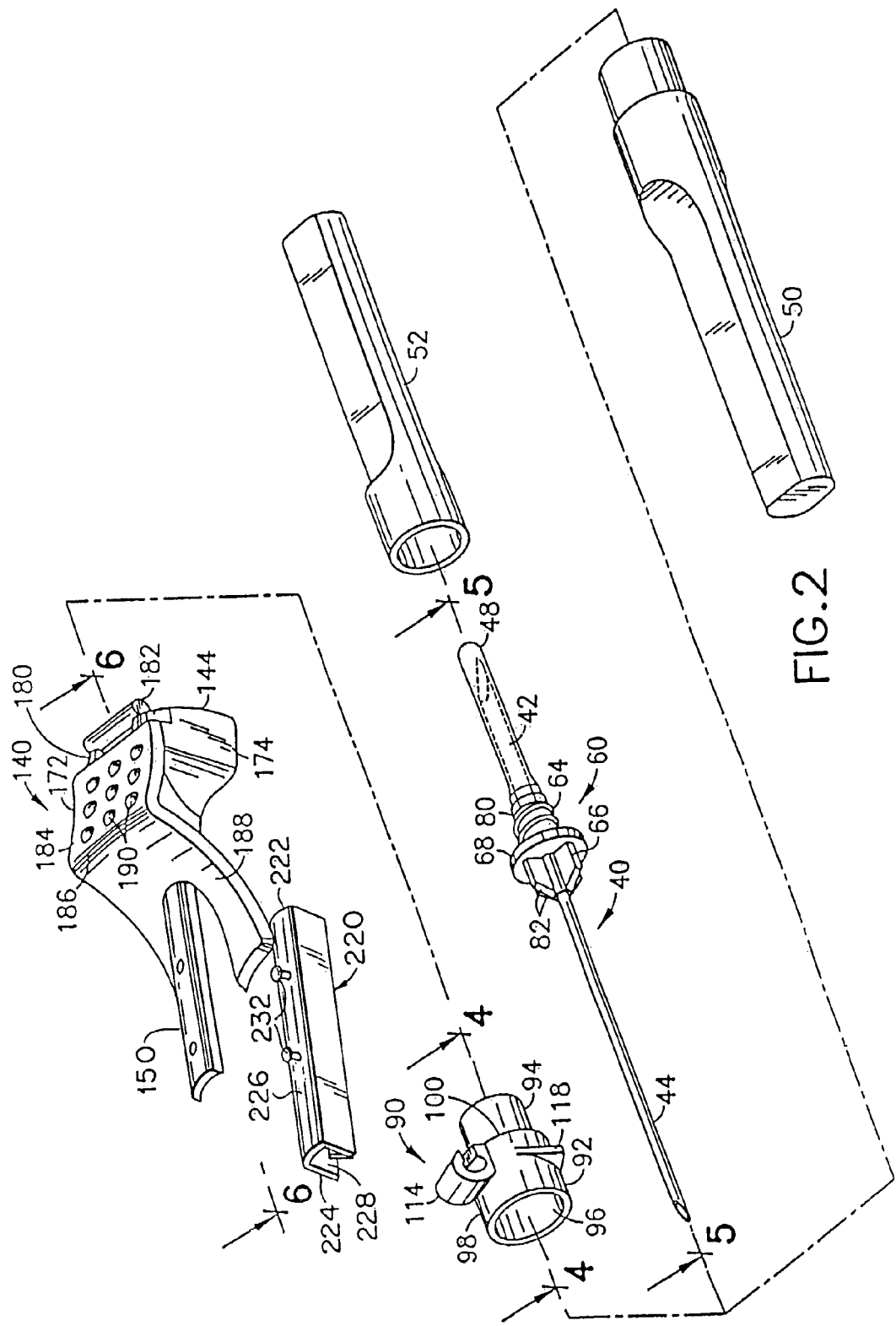

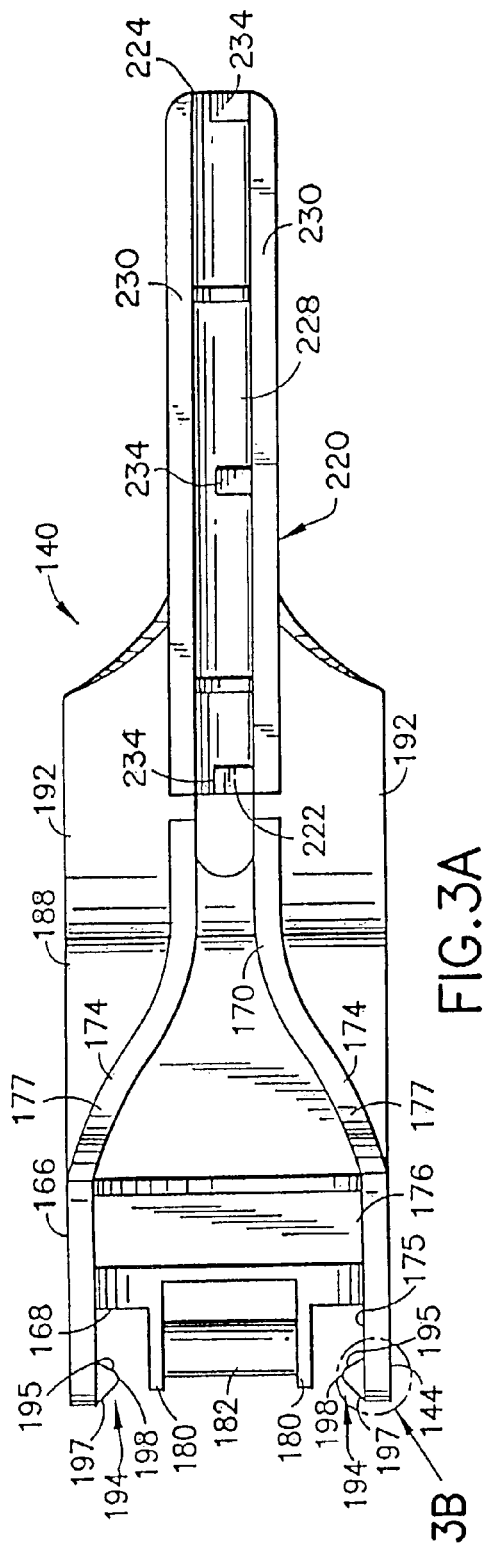
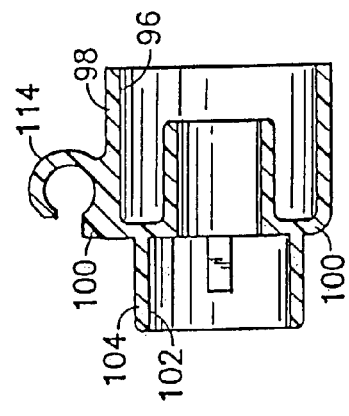
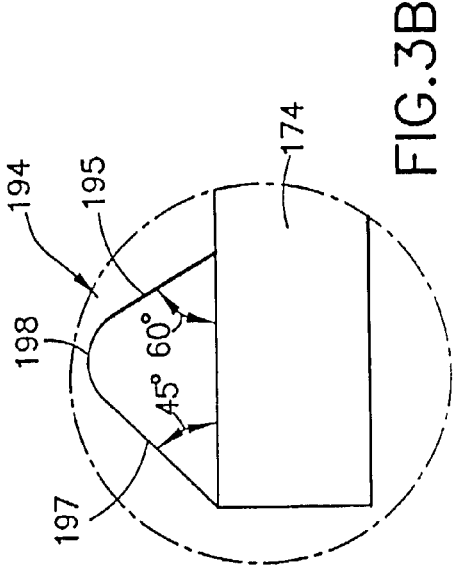

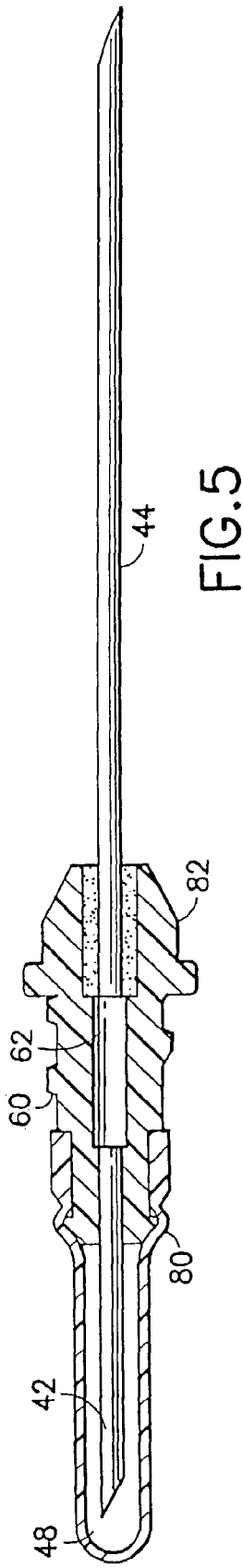
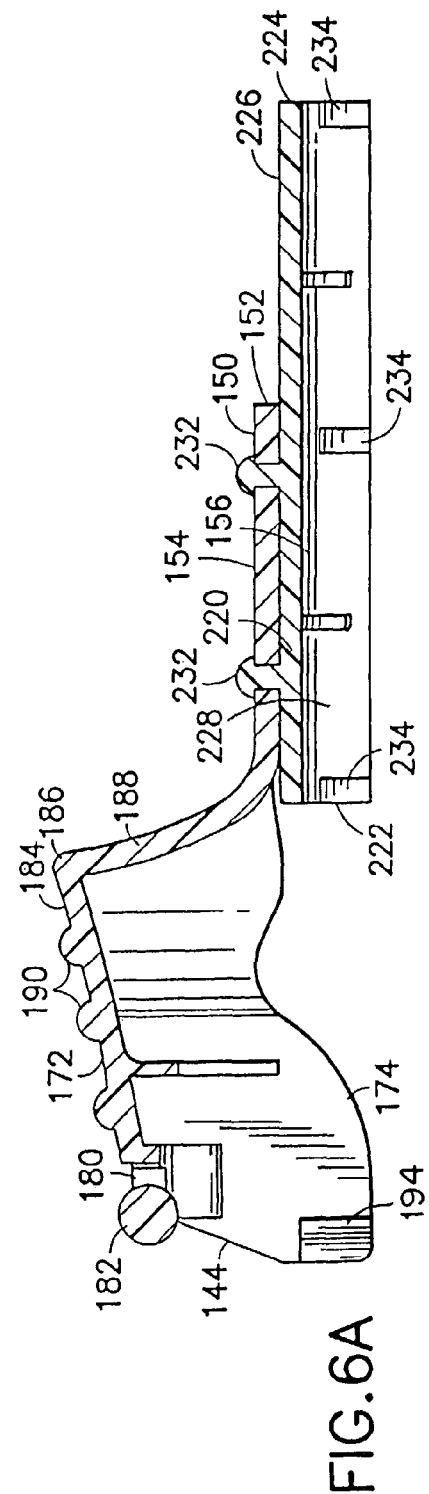

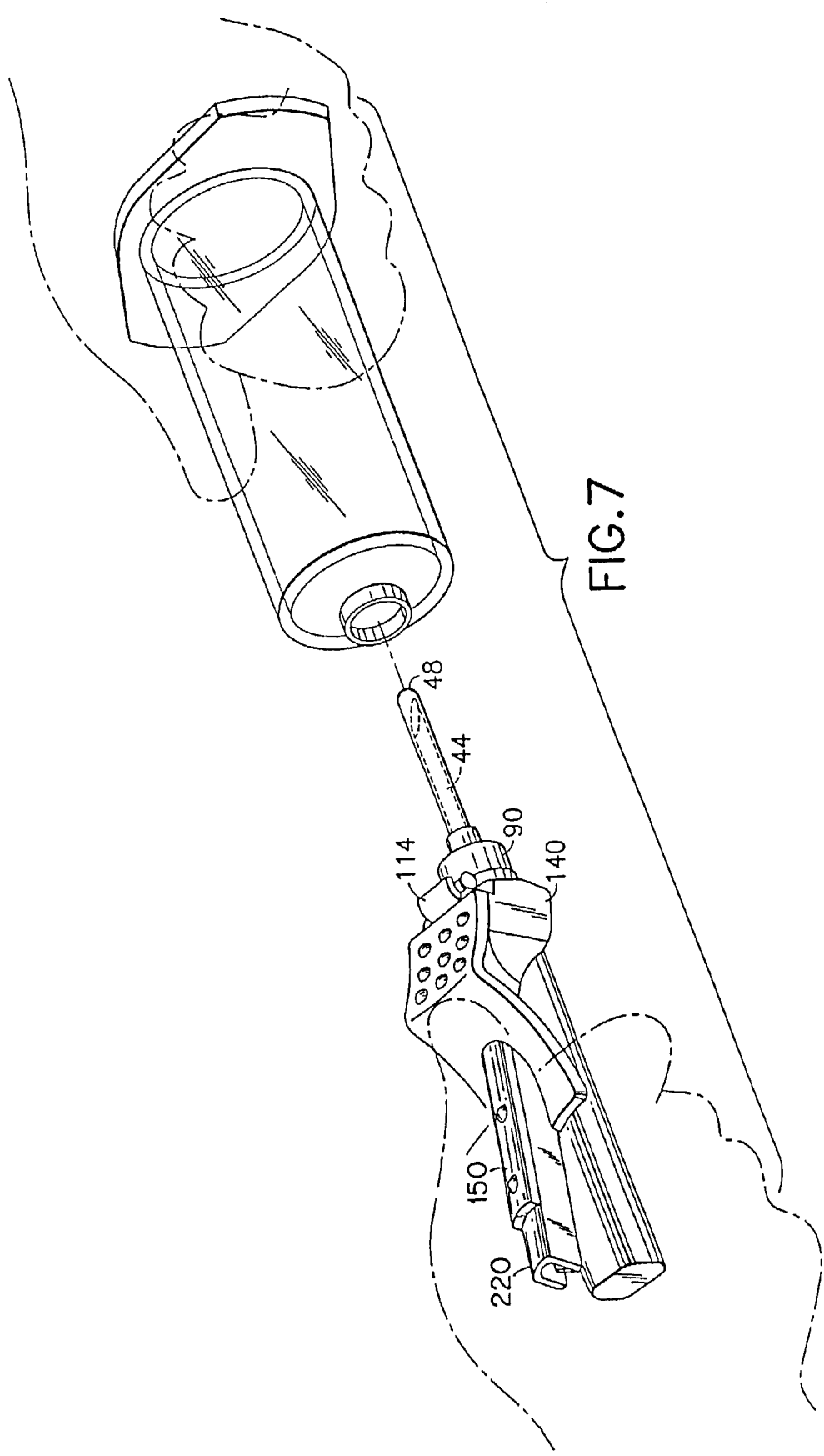

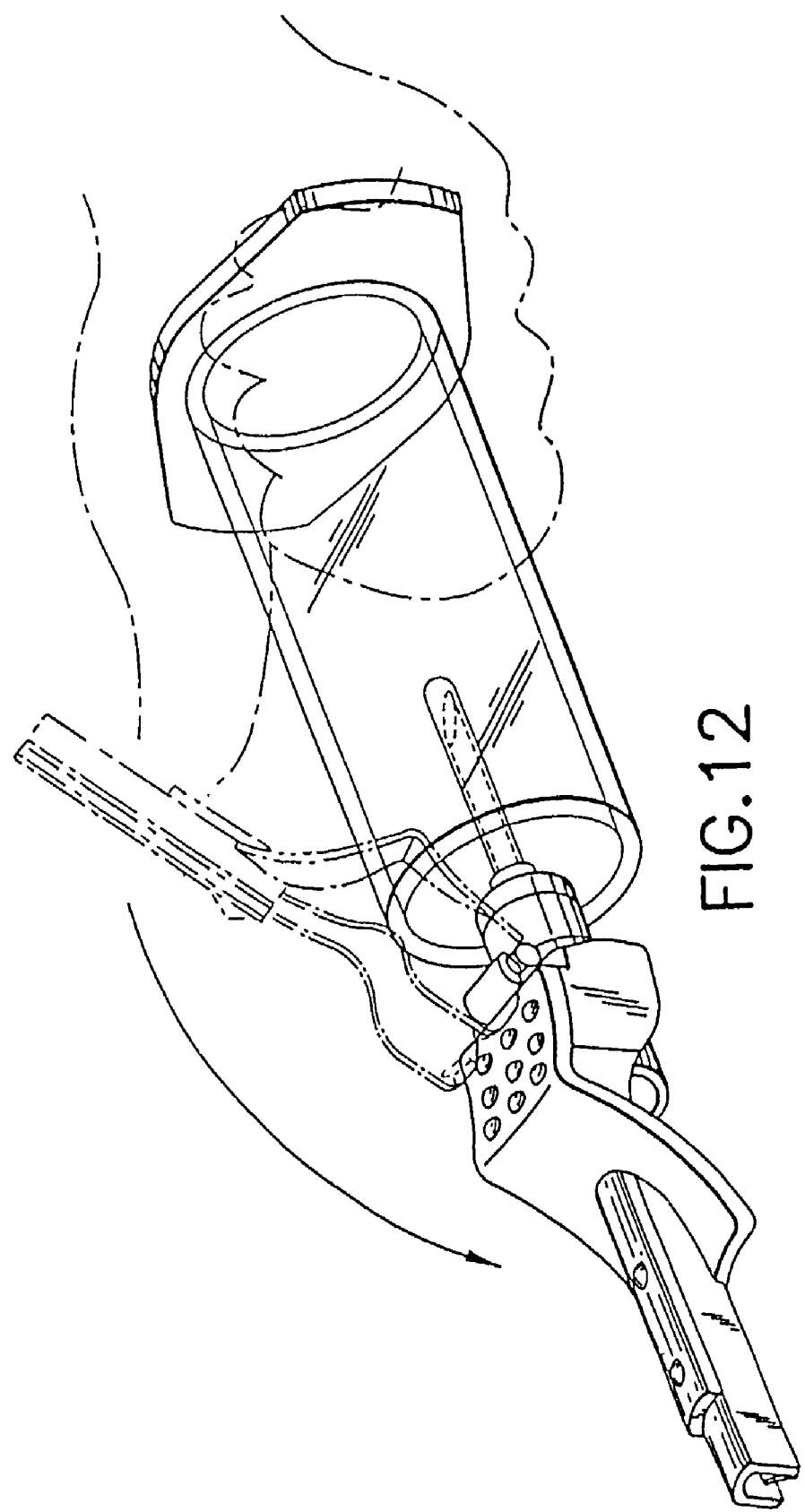

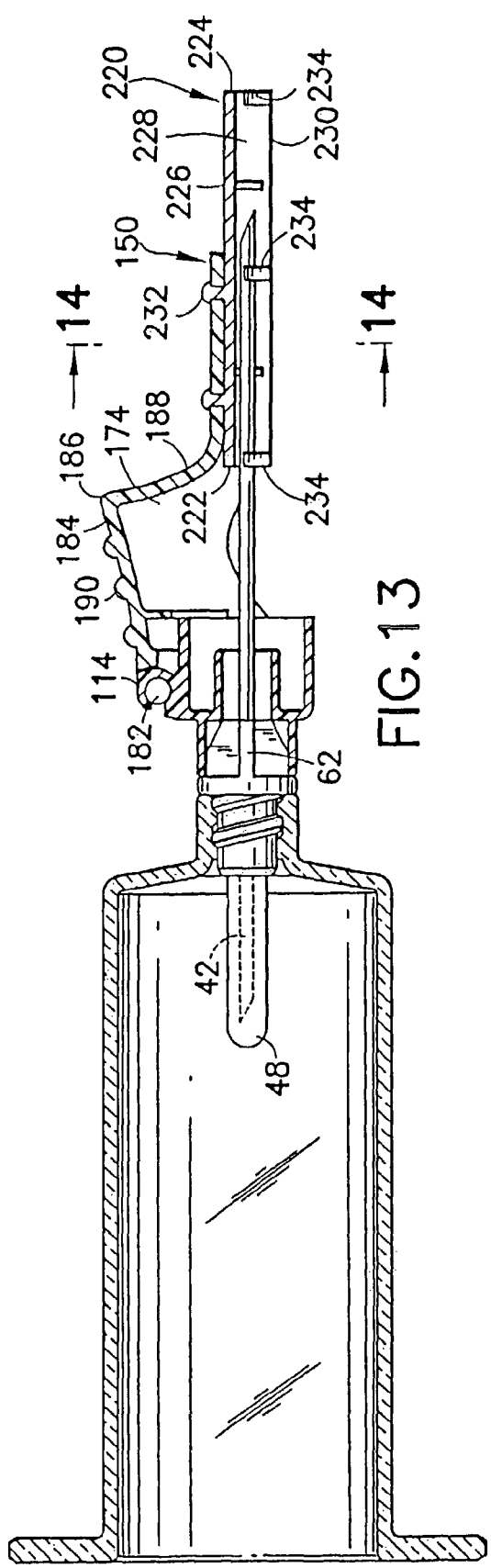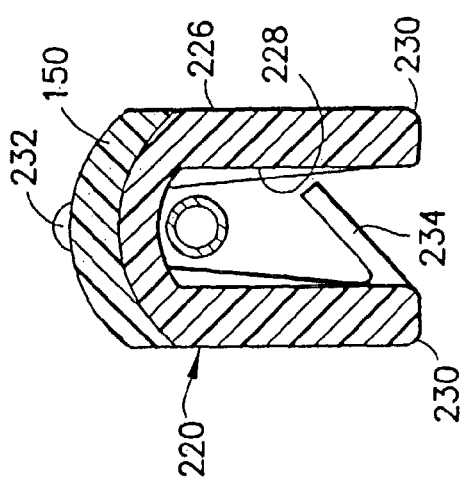

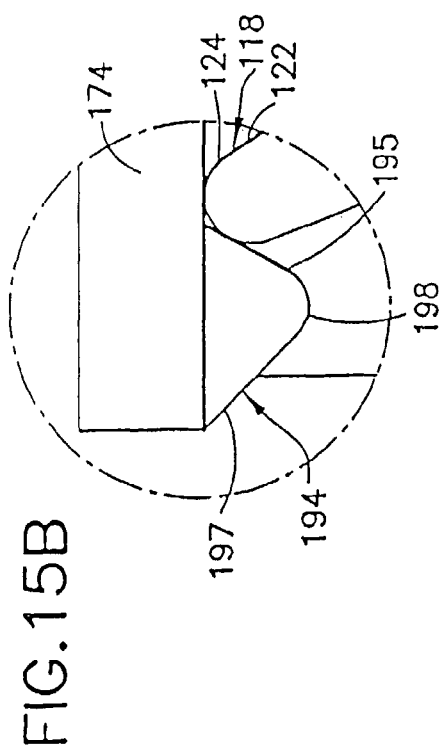
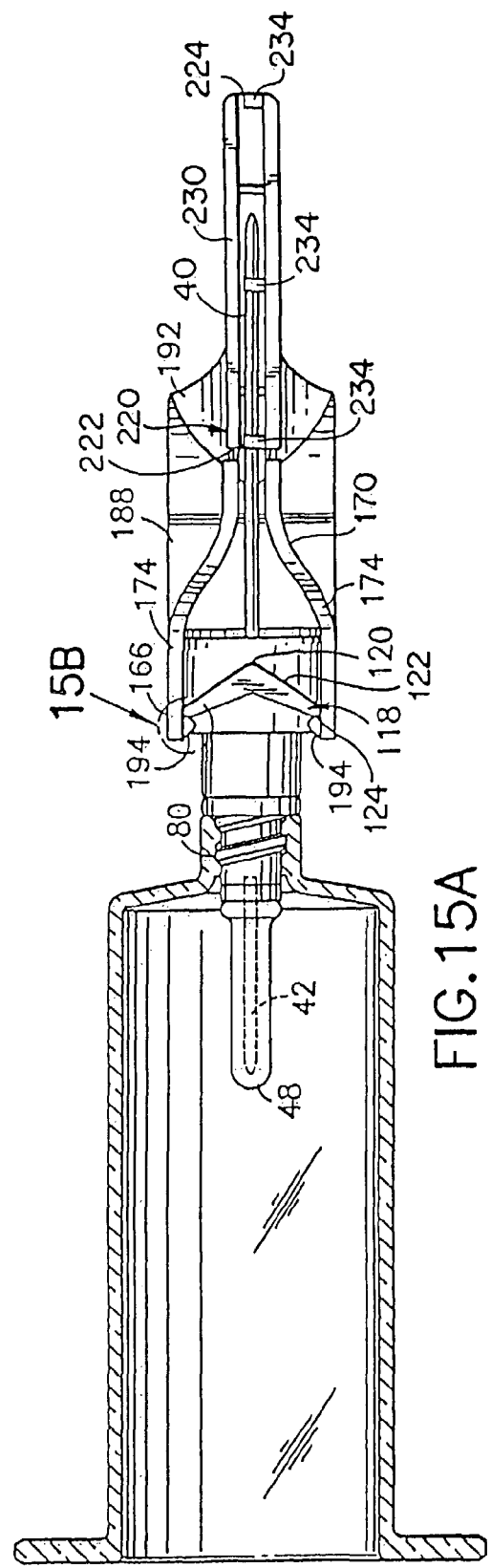

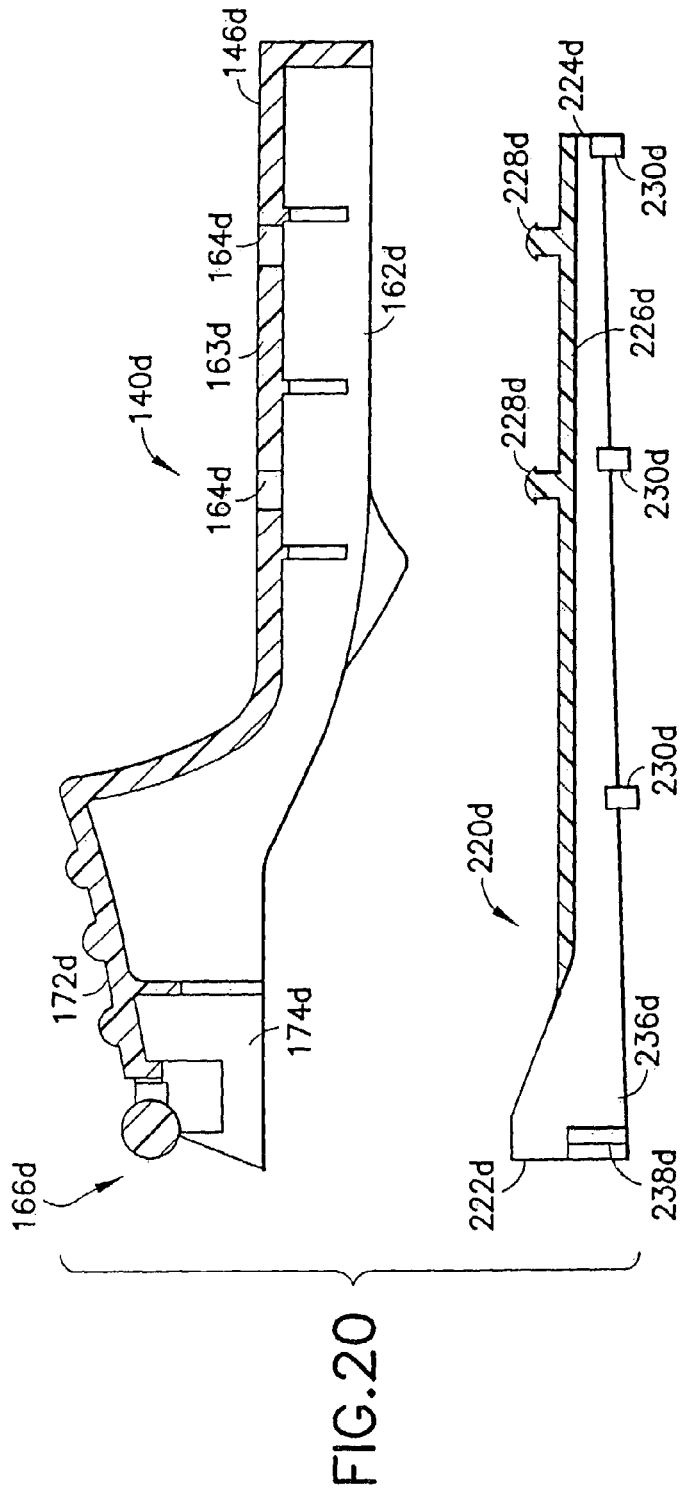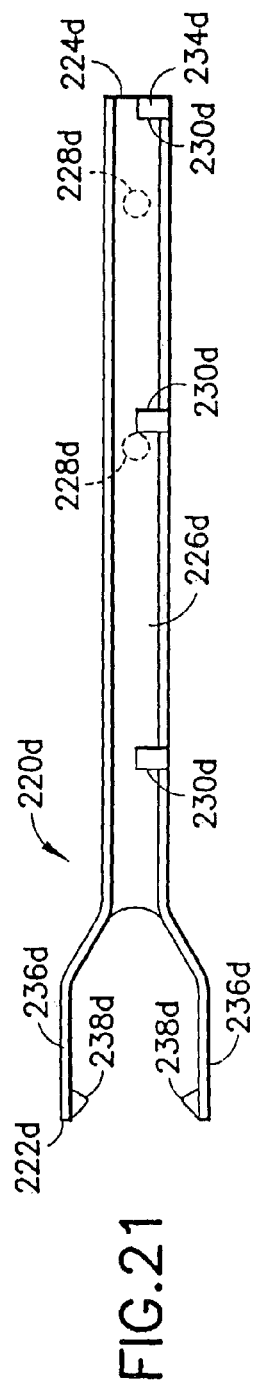

SAFETY NEEDLE ASSEMBLY

RELATED APPLICATION

This application is a continuation of U.S. patent application Ser. No. 10/173,239, filed Jun. 14, 2002.

FIELD OF THE INVENTION

The present invention relates to a shield for a needle and more particularly to a safety shield assembly that may be used in conjunction with a syringe assembly, a hypodermic needle, a needle assembly, a needle assembly with a needle holder, a blood collection needle, a blood collection set, an intravenous infusion set or other fluid handing devices or assemblies that contain piercing elements.

BACKGROUND OF THE INVENTION

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannula or blunt ended cannula.

Safe and convenient handling of disposable medical devices is recognized by those in the medical arts so as to minimize exposure to blood borne pathogens. Safe and convenient handling of disposable medical devices results in the disposal of the medical devices intact.

As a result of this recognition, numerous devices have been developed for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies. For example, some devices employ very short thin needle cannula's. A shield designed to lock near the distal end of one needle cannula might not engage a much shorter needle cannula. Additionally, a shield designed to lock with a wider gauge needle cannula might be more likely to generate a spray upon engaging a much narrower needle cannula. Furthermore, it may be desirable to reduce the force required to effect shielding without reducing the audible and tactile indications of complete shielding.

Therefore, there exists a need for a safety shield assembly: (i), that is manufactured easily; (ii) that is applicable to many devices; (iii) that is simple to use with one hand; (iv) that can be disposed of safely; (v) that does not interfere with normal practices of needle use; (vi) that has tactile features whereby the user may be deterred from contacting the needle, the user may easily orient the needle with the patient and easily actuate and engage the shield assembly; (vii) that has visual features whereby the user may be deterred from contacting the needle, the user may easily orient the needle with the patient and easily actuate and engage the shield assembly; (viii) that is not bulky; (ix) that includes means for minimizing exposure to the user of residual fluid leaking from the needle; and (x) provides minimal exposure to the user because the needle shield is immediately initiated by the user after the needle is withdrawn from the patient's vein.

SUMMARY OF THE INVENTION

The present invention is a safety shield assembly that comprises: a shield; means for connecting the shield to a fluid handling device that contains a piercing element, such as needle; means for pivoting the shield away from the needle; and means for securely covering and/or containing the needle within the shield.

Preferably, the shield comprises a rearward end, a forward end, a slot or longitudinal opening for housing the used needle in the forward end, means for securing the needle in the slot, means for guiding the needle into the slot, means for connecting the shield and the fluid handling device, means for guiding the user's fingers to move the shield into various positions, and means for retaining the shield securely over the used needle.

Desirably, the means for connecting the shield to the fluid handling device is a collar. Preferably, the shield is connected movably to a collar which is connected to a fluid handling device.

Preferably, the shield is connected to the collar by a hanger bar that engages with a hook arm on the collar so that the shield may be pivoted with respect to the collar into several positions. It is within the purview of the present invention to include any structure for connecting the shield to the collar so that the shield may be pivoted with respect to the collar. These structures include known mechanical hinges and various linkages, living hinges, or combinations of hinges and linkages.

Most preferably, the shield is connected to the collar by an interference fit between the hanger bar and the hook bar. Therefore, the shield always is oriented in a stable position and will not move forward or backwards unless movement of the shield relative to the hanger bar and the hook bar is initiated by the user.

Alternatively, the collar and at least a portion of the shield may be a unitary one-piece structure. The one-piece structure may be obtained by many methods, including molding the shield and the collar as a one-piece unit, thereby eliminating the separate shield and collar during the manufacturing or assembly process.

The assembly of the present invention may further comprise tactile and visual means for deterring the user from contacting the needle, providing easy orientation of the needle with the patient and providing the user with a guide for actuation and engagement with the shield.

The assembly of the present invention may further comprise means for minimizing exposure by the user to residual fluid leaking from a used needle. For example, a polymer material, such as a gel, may be located in the shield.

Most desirably, the assembly of the present invention is such that the cooperating parts of the assembly provide the means for the shield to move into a forward position over the needle. Thus, by simple movement of the shield into a forward position over the used needle, the assembly is ready for subsequent disposal. Therefore, the safety shield assembly of the present invention provides minimal exposure of the user to a needle because the shielding is initiated by the user immediately after the needle is withdrawn from the patient's vein.

Desirably, the assembly of the present invention may be used with a syringe assembly, a hypodermic needle, a needle assembly, a needle assembly with a needle holder, a blood collection set, an intravenous infusion set or other fluid handling devices. Preferably, the assembly of the present invention is used with a needle assembly comprising a needle and a hub. Preferably the needle is a conventional double ended needle.

Most preferably, the present invention is used with a needle assembly comprising a hub and a needle connected to the hub whereby the needle comprises a non-patient end and an intravenous end. The collar of the present invention may comprise a hook arm and the shield may be connected movably to the hook arm. Thus the shield may be pivoted with respect to the collar and moved easily into several positions.

Preferably, the collar is fitted non-rotatably with the hub of the needle assembly. Additionally, the collar includes cooperating means that mate with reciprocal means on the shield to provide a clear audible and tactile indication of shielding. The cooperating means on the collar may include generally chevron-shaped, projection formed on a side of the collar substantially diametrically opposite the hook arm or other such structure that provides the hinge connection to the shield. The chevron-shaped structure includes a forward or distal point. Slanting surfaces diverge and extend proximally from the distal point. The slanting surfaces cooperate with the reciprocal means on the shield to generate a deflection of the sidewalls of the shield away from one another. The chevron-shaped structure further includes proximal ends that are convexly arcuate. The convexly arcuate ends of the chevron-shaped structure on the collar cooperate with the reciprocal means on the shield and with the resiliently deflectable sidewalls of the shield to generate the tactile and audible indication of shielding.

The shield preferably includes a proximal or rearward portion that is hingedly connected to the collar and a distal or forward portion that comprises, a support extending unitarily from the rearward portion of the shield. The shield may further comprise a cannula channel securely mounted to at least the support of the forward portion. The channel may comprise a top wall securely connected to the support of the shield and a pair of opposed spaced apart sidewalls extending downwardly from the top wall. The spacing between the sidewalls is selected to accommodate the needle cannula in the channel. At least one of the sidewalls of the cannula channel is formed with at least one cannula finger lock that projects angularly toward the top wall of the cannula channel. The cannula finger lock is dimensioned, disposed and aligned to contact the needle cannula when the shield approaches the second position. Contact between the needle cannula and the cannula finger lock will cause the cannula finger lock to resiliently deflect toward the sidewall from which the cannula finger lock extends. Sufficient rotation of the shield will cause the needle cannula to pass the cannula finger lock. As a result, the cannula finger lock will resiliently return to or toward its undeflected condition for securely trapping the needle cannula in the shield.

The top wall of the cannula channel may comprise means for engaging reciprocal means on the support of the forward portion of the shield. The mounting means on the cannula channel may be disposed in a non-central position relative to the longitudinal direction of the channel. Thus, the cannula channel can be mounted to the shield support in either of two alternate orientations that are rotated 180° from one another. In a first rotational orientation, the cannula channel projects distally or forwardly beyond the support of the shield. In a second rotational orientation, the cannula channel projects rearwadly or proximally from the support of the shield to overlie the rearward portion of the shield. Thus, the first rotational orientation of the cannula channel ensures that the pointed distal end of a long needle cannula is surrounded by the cannula channel and engaged by the cannula finger locks. The second rotational orientation of the cannula channel ensures that a shorter needle cannula is surrounded by the cannula channel and engaged by the cannula finger locks.

The cannula channel may have a proximal or rear end configured for engaging the collar or hub when the shield is in its second position. Engagement of the channel with the collar or hub may contribute to locked retention of the shield in the second position. Additionally, engagement of the proximal end of the cannula channel with the collar or hub may further support the channel and prevent excessive deformation of the channel.

Preferably, the collar is fitted with the hub of the needle assembly so that the collar cannot rotate around the hub. Alternatively, the collar and hub may be a unitary one-piece structure. The one piece structure may be accomplished by many methods including molding the collar and the hub as a one-piece unit:thereby eliminating the need to separately assemble the collar to the hub during the manufacturing process.

Most preferably, the collar is fitted with the hub of the needle assembly so that the bevel surface or bevel up surface of the intravenous or distal end of the needle faces the same side of the collar when the shield is in the first position. Alignment of the collar, hub, shield and needle with the bevel surface up makes it easier to insert the needle into the patient without manipulating the assembly. The orientation of the intravenous end of the needle with the bevel up assures the user that the needle is properly oriented for use and does not require any manipulation before use. Most notably, the orientation of the shield provides a visual indication to the user of the orientation of the bevel surface of the needle.

Preferably, the shield is capable of pivoting from a first position where the intravenous end of the needle is exposed and bevel up, to an intermediate position where the needle is partially covered, to a second position where the needle is covered completely.

Alternatively, it is within the purview of the present invention that the collar, hub and at least a portion of the shield may be a unitary one-piece structure. The one-piece structure may be accomplished by many methods including molding the shield, collar and hub as a one-piece unit thereby eliminating the need to separately assemble the shield, collar and hub during the manufacturing process.

It is an advantage of the present invention that the shield covering the used intravenous end of the needle provides easy containment of the used needle. A further advantage of the shield is that it will only move upon initiation by the user.

The assembly of the present invention when used with a fluid handling device is also easily disposable when removed from a conventional needle holder, or other such device.

A notable attribute of the present invention is that it is easily adaptable with many devices. For example, the invention is usable with syringe assemblies, hypodermic needles, needle holders, blood collection needles, blood collection sets, intravenous infusion sets such as catheters or other fluid handling devices or assemblies that contain piercing elements.

Another notable attribute of the present invention is that the tactile and visual features deter the user from touching the needle, allow the user to easily orient the needle with the patient and guide the user to actuate and engage the shield of the assembly.

BRIEF DESCRIPTION OF THE DRAWINGS

FIG. 1 is a perspective view of the safety shield assembly of the present invention as connected to a needle assembly and related packaging features.

FIG. 2 is a perspective view of the unassembled pieces of FIG. 1.

FIG. 3A is a bottom view of the shield as shown in FIG. 2.

FIG. 3B is an enlarged bottom view of an ear of the shield.

FIG. 4 is a cross sectional view of the collar as shown in of FIG. 2 taken along lines 4-4 thereof.

FIG. 5 is a cross sectional view of the needle hub as shown in FIG. 2 taken along lines 5-5 thereof.

FIG. 6A is a cross sectional view of the shield of FIG. 2 taken along lines 6A-6A thereof.

FIGS. 7-12 illustrate the use of the safety shield assembly with the needle assembly of FIG. 1 with a conventional needle holder.

FIG. 13 is a cross sectional view of the assemblies in use with a conventional needle holder as shown in FIG. 12 taken along lines 13-13 thereof.

FIG. 14 is a cross-sectional view of the assemblies of FIG. 13 taken along lines 14-14 thereof.

FIG. 15A is a bottom view of the assemblies as shown in FIG. 11.

FIG. 15B is an enlarged bottom view showing the engagement of the ear and the chevron-shaped projection.

FIG. 20 is an exploded side elevational view of an additional embodiment of the present invention.

FIG. 21 is a bottom view of the clip of FIG. 20.

DETAILED DESCRIPTION OF THE INVENTION

Figure 6B:
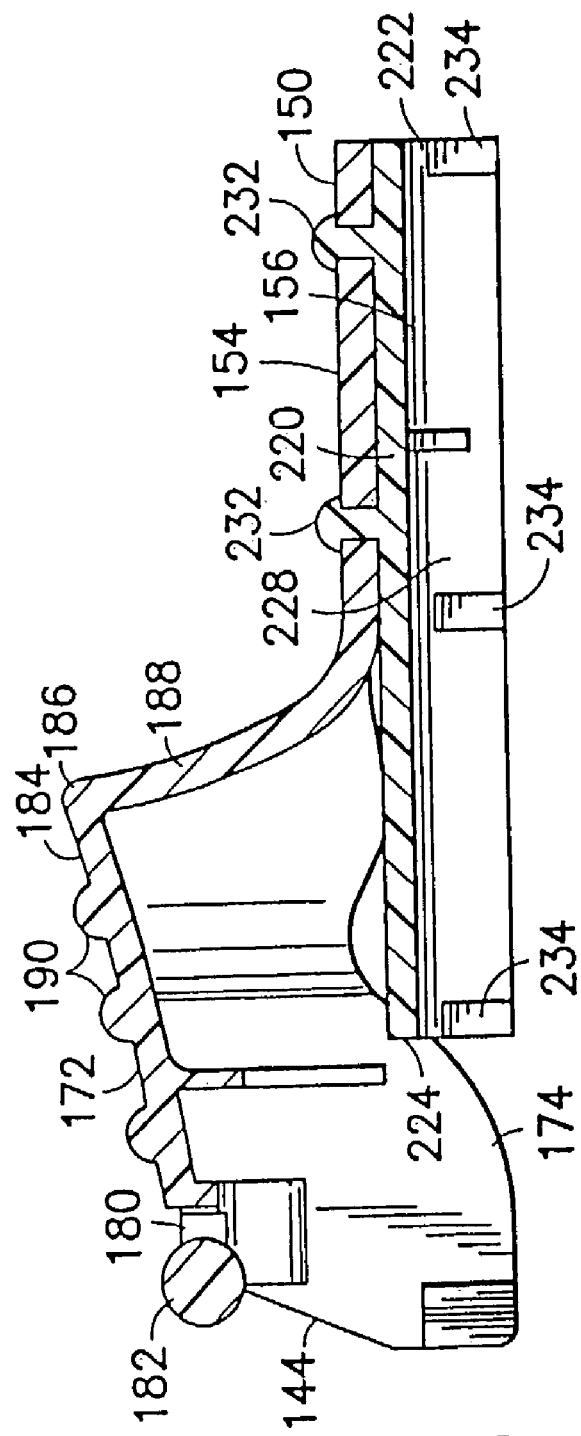
FIGS. 6B is a cross-sectional view similar to FIG. 6A, but showing the cannula channel in an end-to-end reversed orientation.
Figure 8:
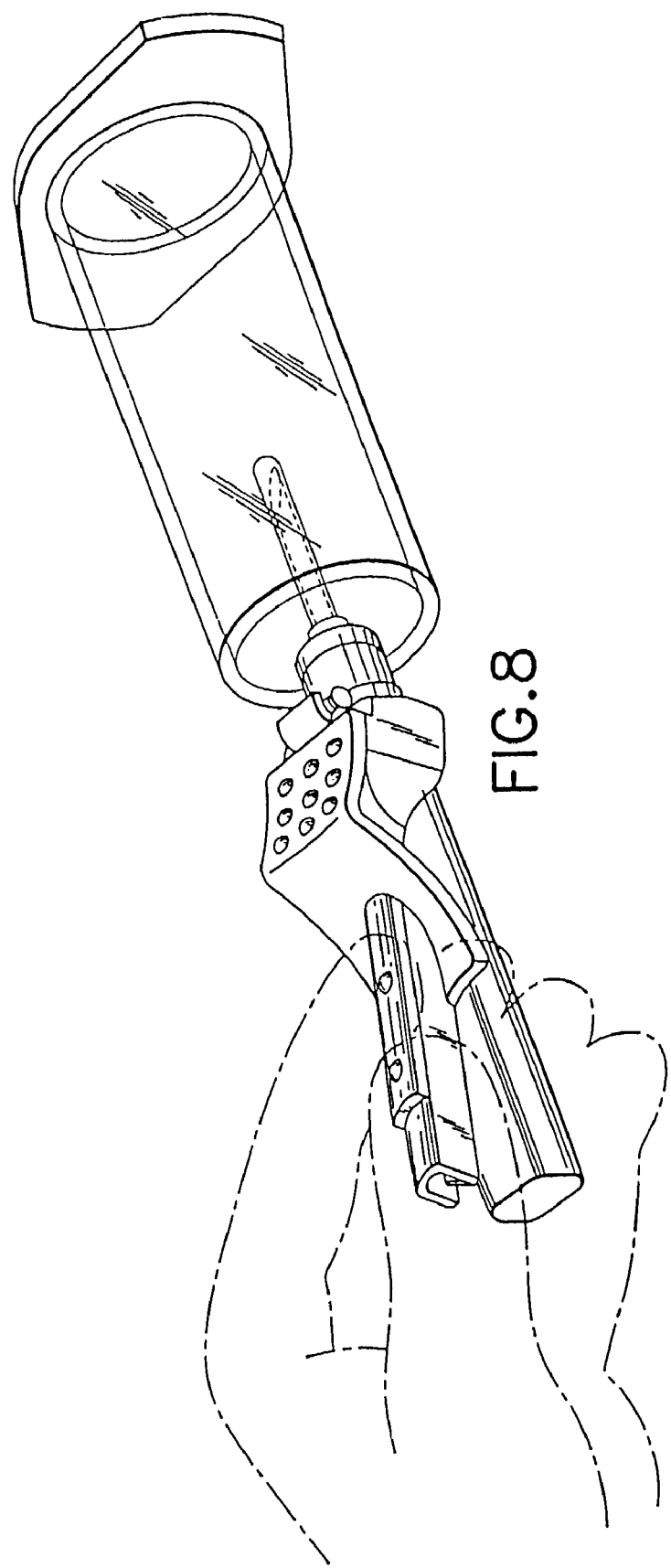

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views-thereof, FIGS. 1 and 2 illustrate a needle assembly with the safety shield assembly of the present invention and the related packaging features. The needle assembly includes a needle 40, a hub 60, packaging features to cover the needle and a label. The safety shield assembly includes a collar 90 and a shield 140.

As shown in FIG. 2 and 5, needle 40 includes a non-patient end 42, an intravenous end 44 and a passageway 46 extending between the non-patient end and the intravenous end. An elastomeric sleeve 48 covers the non-patient end. A first rigid sleeve 50 covers the intravenous end and a second rigid sleeve 52 covers the non-patient end and the elastomeric sleeve. As shown in FIG. 1, a label 196 may also be applied to the finally assembled parts.

As shown in FIGS. 2 and 5, hub 60 includes a threaded end 64, a ribbed end 66 and passageway 62 extending between the threaded end and the ribbed end. Threaded end 64 and ribbed end 66 are separated by flange 68. Non-patient end 42 of needle 40 extends from threaded end 64 and intravenous end 44 of needle 40 extends from ribbed end 66. Preferably, threaded end 64 comprises male threads 80 for mounting the hub on a conventional needle holder and ribbed end 66 comprises male ribs 82 for connecting the hub and collar 90.

As shown in FIGS. 2 and 4, collar 90 includes a forward skirt 92 and a rearward skirt 94. Forward skirt 92 is cylindrical and comprises an inner circumferential surface 96 and an outer circumferential surface 98. Forward skirt 92 mates with rearward skirt 94 at a shoulder 100. Rearward skirt 94 is cylindrical and comprises an inner circumferential surface 102 and an outer circumferential surface 104 and extends from shoulder 100 opposite of forward skirt 92. The inner diameter of forward skirt 92 is larger than the inner diameter of rearward skirt 94. Alternatively, the inner diameters for collar 90 can be equal. A hook 114 extends from outer circumferential surface 98 of forward skirt 92. Additionally a chevron-shaped protrusion 118 projects outwardly from outer circumferential surface 98 of forward skirt 92 at a side opposite hook 114. The chevron-shape protrusion 118 is substantially symmetrical and has a peak 120 pointed toward forward skirt 92 and ramp surfaces 122 that diverge symmetrically from peak 120 toward rearward skirt 94. Ramp surfaces 122 terminate at rounded ends 124 at the outer side and proximal extremes of chevron-shaped protrusion 118. Rounded ends 124 extend continuously into the proximal side of chevron-shaped protrusion 118 facing toward rearward skirt 94.

As shown in FIGS. 2 and 6, shield 140 comprises a rearward end 144 and a forward end 146. Forward end 146 of shield 140 defines an elongate support wall 150 with a distal end 152 and top and bottom surfaces 154 and 156 extending proximally from distal end 152. In the illustrated embodiment, top and bottom surfaces 154 and 156 are slightly arcuate from side-to-side. However, in other embodiments, top surface 154 and/or bottom surface 156 may be substantially planar. Support wall 152 is characterized by axially spaced apertures 158 extending entirely therethrough from top surface 154 to bottom surface 156.

Rearward end 144 of shield 140 defines a collar engaging area 166. Collar engaging area 166 includes a rearward end 168, a forward end 170, a top finger guide area 172, sidewalls 174 that extend downwardly from top finger guide area 172, an underside area 176 dimensioned for surrounding collar 90, and extending arms 180 to support hanger bar 182. Sidewalls 174 are spaced apart by a major width adjacent rearward end 168. The major width is selected to enable sidewalls 174 to slide across diametrically opposite side surfaces of forward skirt 92 of collar 90. Sidewalls 174 converge, however, toward forward end 170 to define a minor distance therebetween. Sidewalls 174 include bottom edges 177 that face away from top finger guide area 172. As shown most clearly in FIG. 6, bottom edges 177 curve toward top finger guide area 172 at locations between rearward end 168 and forward end 170 of collar engaging area 166.

Shield 140 further includes a cannula channel 220. Cannula channel 220 includes opposed longitudinal ends 222 and 224, an elongate convex outer surface 226 extending between ends 222 and 224 and an inner concave surface 228 extending between ends 222 and 224. An entry to concave inner surface 228 is defined by opposed parallel edges 230 that extend substantially between ends 222 and 224 of channel 220. Mounting projections 232 project from convex outer surface 226 at a location substantially equally spaced from edges 230. Thus, mounting projections 232 are substantially opposite from the entry into concave inner surface 228 of channel 220. Mounting projections 232 are spaced from one another by a distance substantially equal to the spacing between mounting apertures 158 in support wall 150. Additionally, mounting projections 232 are dimensioned to be snapped or force fit into apertures 158. Mounting projections 232 are not symmetrically disposed along the length of cannula channel 220. Rather, mounting projections 232 are closer to end 222 than to end 224. Channel 220 is defined further by cannula finger locks 234 that project obliquely inwardly from one of side edges 230. Cannula finger locks 234 are resiliently deflectable in response to forces exerted by needle 40 as explained further below.

The extreme rear ends of sidewalls 174 on collar engaging area 166 include rounded ears 194 that project toward one another from opposed inner surfaces 175 of sidewalls 174. Rounded ears 194 are disposed to engage chevron-shaped projection 118 on collar 90. More particularly, each rounded ear 194 includes a distal surface 195, a proximal surface 197 and a curved surface 198 extending between distal and proximal surfaces 195 and 197. Distal surface 194 is aligned to sidewall 174 at a rake angle of approximately 60° and proximal surface 197 is aligned to sidewall 174 at an angle of approximately 45°. Curved surface 198 extends smoothly and convexly between distal and proximal surfaces 195 and 197. Proximal surfaces 197 of rounded ears 194 will engage ramp surfaces 122 of chevron-shaped projection 118 to deflect sidewalls 174 slightly away from one another as shield 140 approaches the second position. The apex of curved surface 198 on each rounded ear 194 passes the respective rounded end surface 124 on chevron-shaped projection 118 on collar 90. As a result, sidewalls 174 begin to return resiliently toward an undeflected condition. The resilient return of sidewalls 174 and raked distal surface 195 of ears 194 causes sidewalls 174 to snap against chevron-shaped projection 118. This snapping action provides a clear audible and tactile indication of complete shielding and occurs substantially when the used needle is trapped by cannula finger locks 234. The angles of distal and proximal surfaces 195 and 197 of rounded ears 194 affects the performance of shield 140. In particular, a smaller acute angle alignment of proximal face 197 reduces the force required to move shield 140 passed rounded ears 194. A larger acute angle proximal surface 197 of rounded ears 194 requires a greater force to move shield 140 toward the second position. Similarly, the angle between distal surface 195 and sidewall 174 affects the acceleration characteristics as shield 140 is propelled toward the second position in response to the resilient return of sidewalls 174. This change in acceleration characteristics affects the audible indication of shielding. Different audible and acceleration characteristics can be achieved by employing more sharply pointed corners on the end surface of chevron-shaped projection 118 for engagement by rounded ears 194 of shield 140.

Top finger guide area 172 comprises a first ramp 184 that extends slightly on an upwardly slope from the rearward end of the collar engaging area to a shoulder 186. From shoulder 186 extends a second ramp 188 which slopes downwardly towards support wall 150. Most preferably, first ramp 184 comprises touch bumps 190. The touch bumps provide a tactile and visual guide to alert the user that the user's finger has contacted the shield and that the shield is in a defined or controlled position. The touch bumps many be any configuration so long as they extend and are distinct from the top finger guide area. The touch bumps may also be of a distinguishing color as compared to the top finger guide area or the shield.

Second ramp 188 has interior surface 192 for urging the needle toward the center as the shield is being rotated into the closed position. The exterior surfaces are slightly inclined and extending radially from the second ramp. The interior surfaces are especially helpful if the longitudinal axis of the needle is misaligned with respect to the longitudinal axis of the hub.

Extending arms 180 are located at rearward end 168 and at the beginning of top finger area 172 and hold hanger bar 182.

The safety shield assembly and the needle assembly are assembled together whereby needle 40 is connected to hub 60 and sealed with adhesive at the ends of the hub. Hub 60 is then joined with collar 90 by ultra-sonic welding techniques or any other bonding techniques, or mechanical fit, whereby rearward annular skirt 94 of collar 90 mates with ribbed end 66 of the hub. Male ribs 82 of the hub are contained or forced fitted within inner sidewall 102 of rearward annular skirt 94 of collar 90. The collar is aligned with the intravenous end of the needle whereby the hook arm is aligned with the bevel up of the needle. Then rigid sleeve 50 is force fitted into inner side wall 96 of forward skirt 92 of collar 90 to cover the needle. Channel 220 then is mounted to support wall 150. More particularly, as shown in FIGS. 2, 3 and 6A, channel 220 is oriented such that end 224 of channel 220 projects distally or forwardly beyond support wall 150. This orientation is appropriate in situations where it is known that a relatively long needle cannula will be employed with the needle assembly. Alternatively, however, channel 220 can be oriented as shown in FIG. 6B so that end 222 of channel 220 is aligned substantially with the distal end 152 of support wall 152 while end 224 of channel 222 projects rearwardly or proximally into rearward end 144 of shield 140. Thereafter, shield 140 is connected to collar 90 whereby hanger bar 182 is force fitted into hook member 114 whereby slot 160 faces rigid sleeve 50. Most preferably, the shield is connected to the collar by a force fit or interference fit between the hanger bar and the hook bar. Therefore, the shield is always oriented in a stable position and will not move unless movement of the shield is positively initiated by the user. To assemble the last piece, shield 140 is moved towards rigid sleeve 50 and second rigid sleeve 52 is force fitted onto outer sidewall 104 of rearward skirt 94 of collar 90.

In addition, a label 196 may be applied to the finally assembled parts. The label may be used to prevent tamper resistance of the parts, so that they are not reused.

Figure 9:
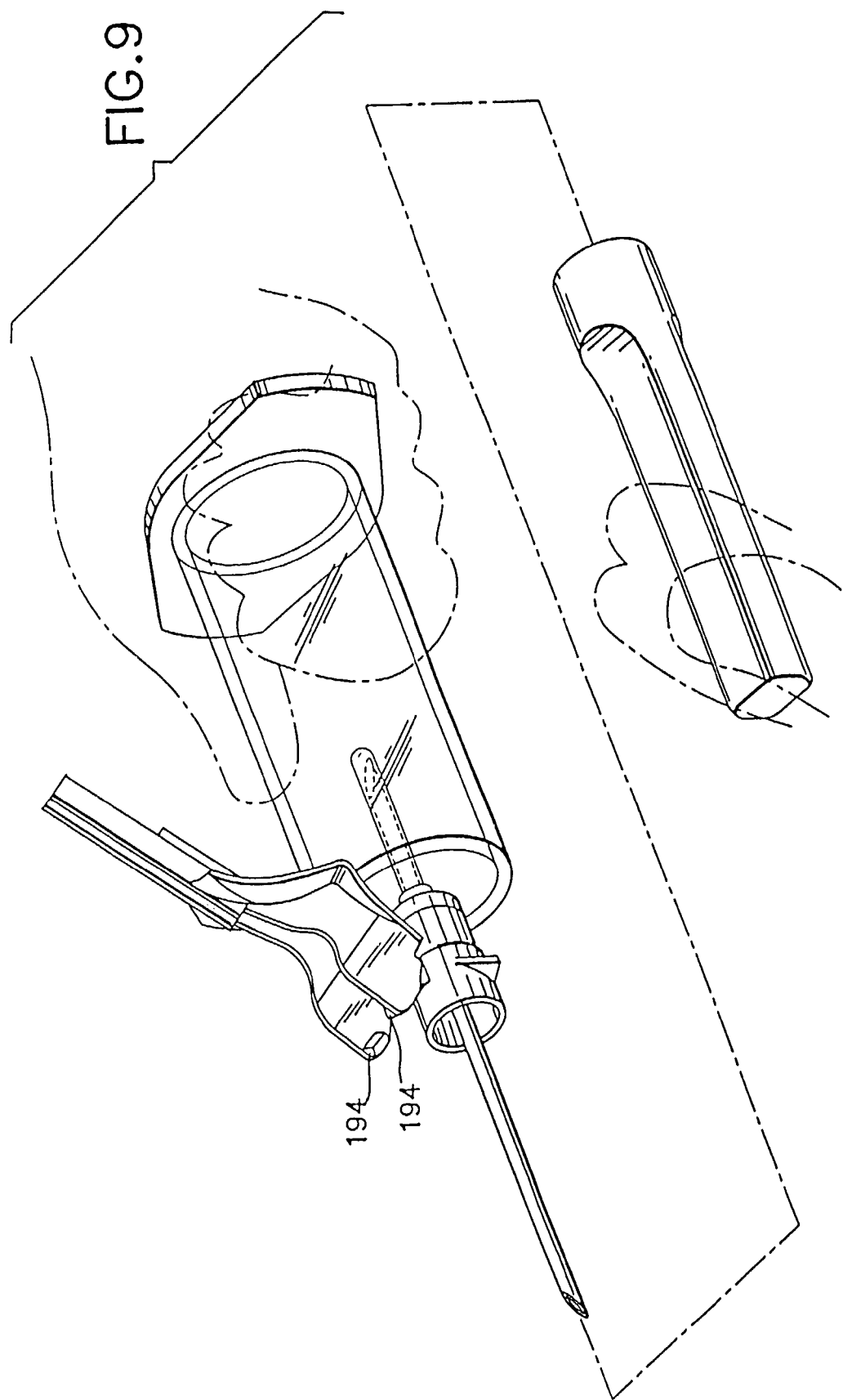
Figure 10:
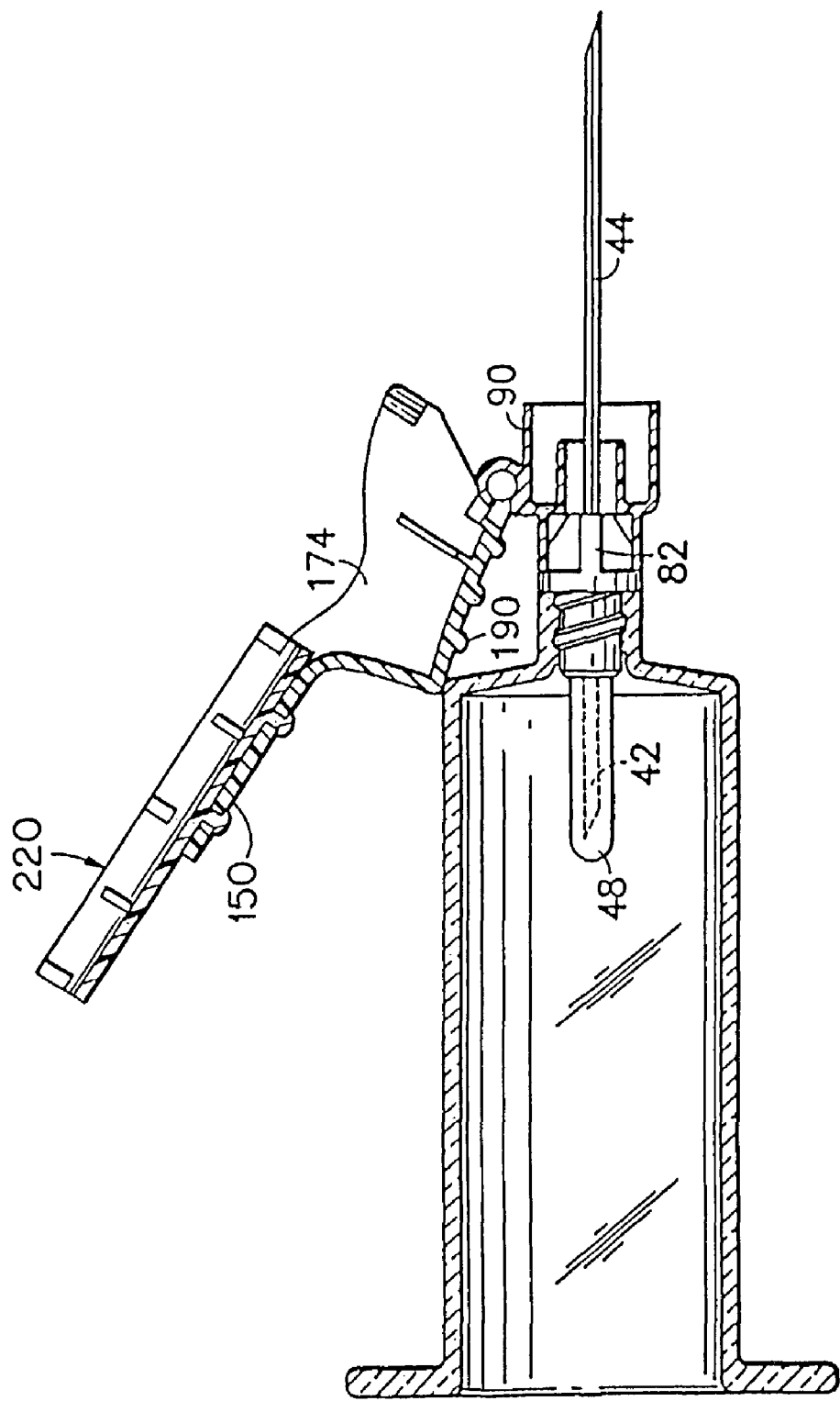
Figure 11:
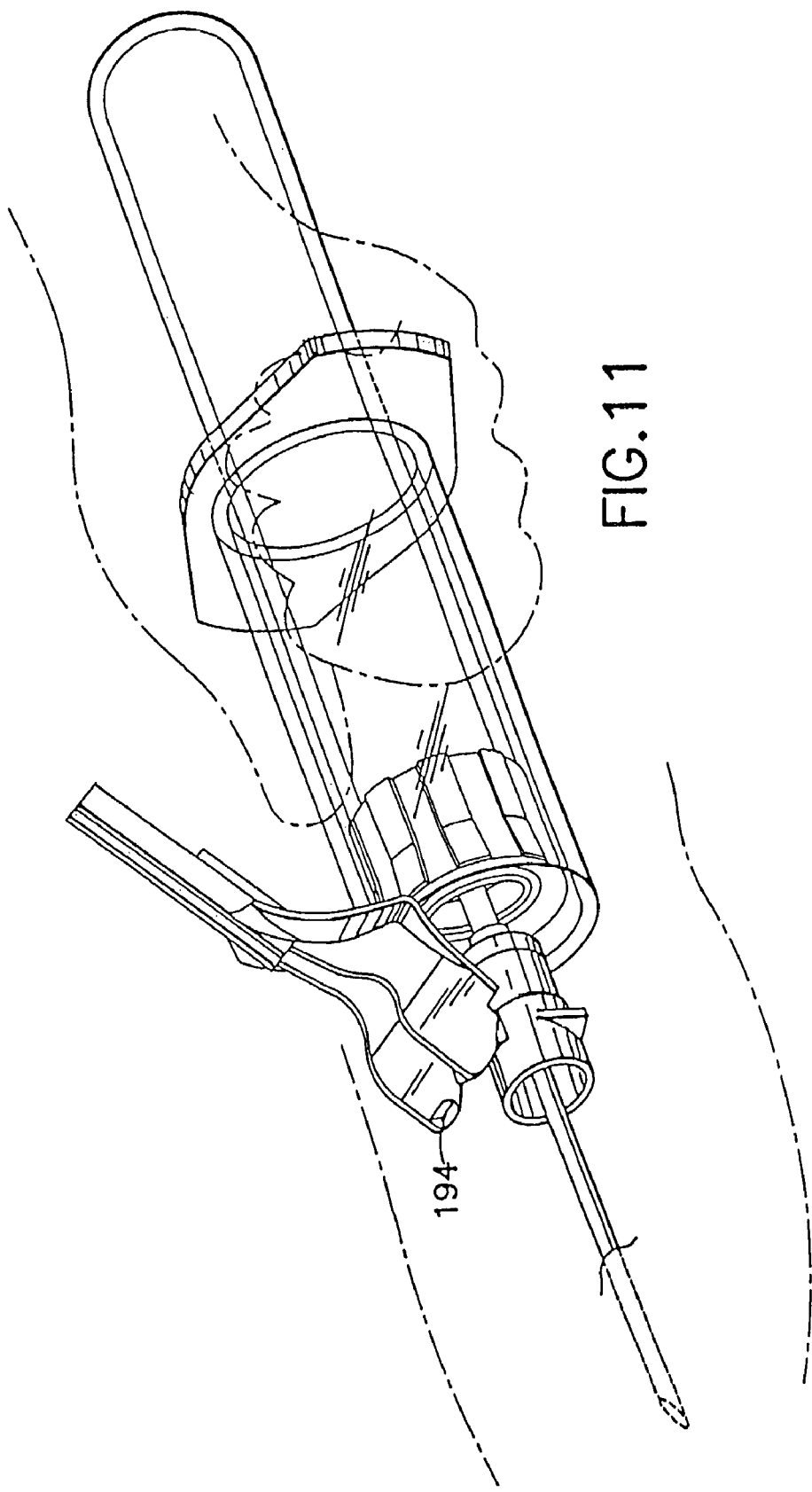
Figure 16:
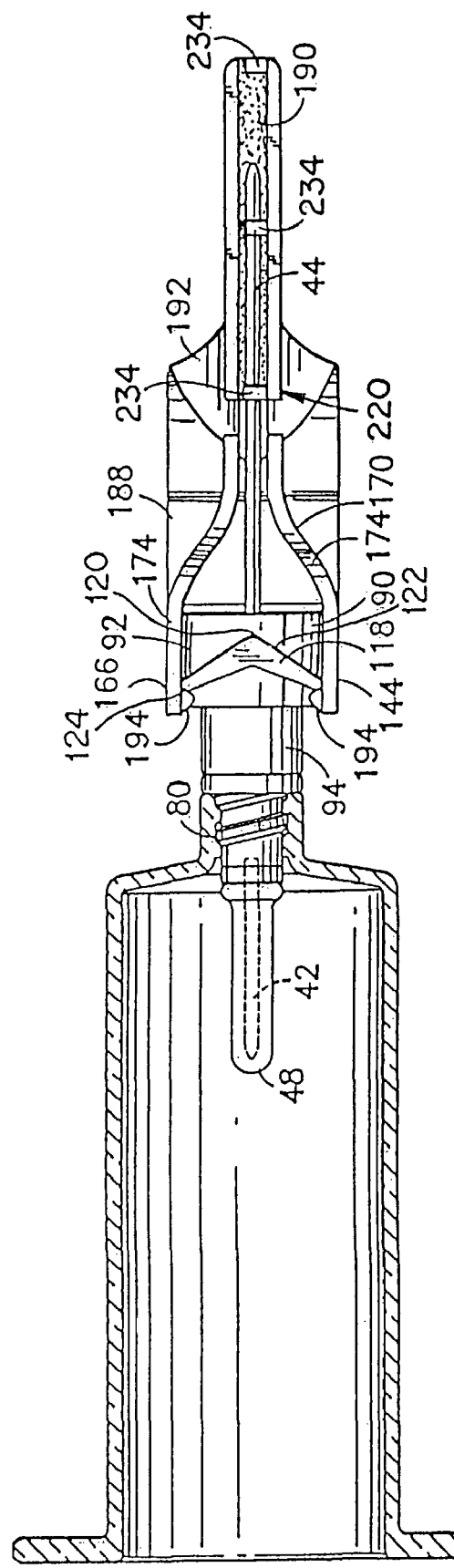
FIG. 16 illustrates an additional embodiment of the present invention, whereby a gel material is located in the shield as shown in a bottom view of the assemblies of FIG. 11.

In use, as shown in FIGS. 7-15, the non-patient needle shield is removed and then a needle holder is screwed onto the hub of the needle. As specifically shown in FIGS. 8 and 12 the shield is then rotated back by the user towards the needle holder. Then as shown in FIG. 9, the intravenous needle shield is removed from covering the intravenous needle. Then as shown in FIG. 10, a venipuncture is conducted whereby the intravenous end of the needle is inserted into a vein of a patient and an evacuated tube having a closure is inserted into the needle holder. Then as shown in FIGS. 11 and 13, when the venipuncture is complete the user easily rotates the shield from the first position towards the intravenous needle to an intermediate position and then the user pushes on the shield at the top finger guide area to move the shield into a second position whereby the needle is trapped in the longitudinal opening. More particularly, needle 40 contacts cannula finger locks 234. Accordingly, cannula finger locks 234 deflect toward support wall 150 and away from edges 230. Sufficient rotation of shield 140 will cause needle 40 to pass cannula finger locks 234. As a result, cannula finger locks 234 will return resiliently to an undeflected condition. Thus, needle 40 will be trapped above cannula finger locks 234.

Needle 40 is contained within shield 140 as the shield is pivoted into the closed position. More particularly, proximal surfaces 197 of rounded ears 194 move over ramp surfaces 122 of chevron-shaped projection 118 and cause sidewalls 174 to deflect away from one another. The angularly aligned proximal faces 197 of rounded ears 194 ensure easy movement of shield 140. Additionally, the resiliency of sidewalls 174 and the angular alignment of distal surface 195 of ears 194 causes a cooperation with rounded proximal ends 124 of chevron-shaped projection 118 to accelerate shield 140. This accelerated movement of shield 140 helps to generate a clear audible and tactile indication of complete shielding.

Figure 17:
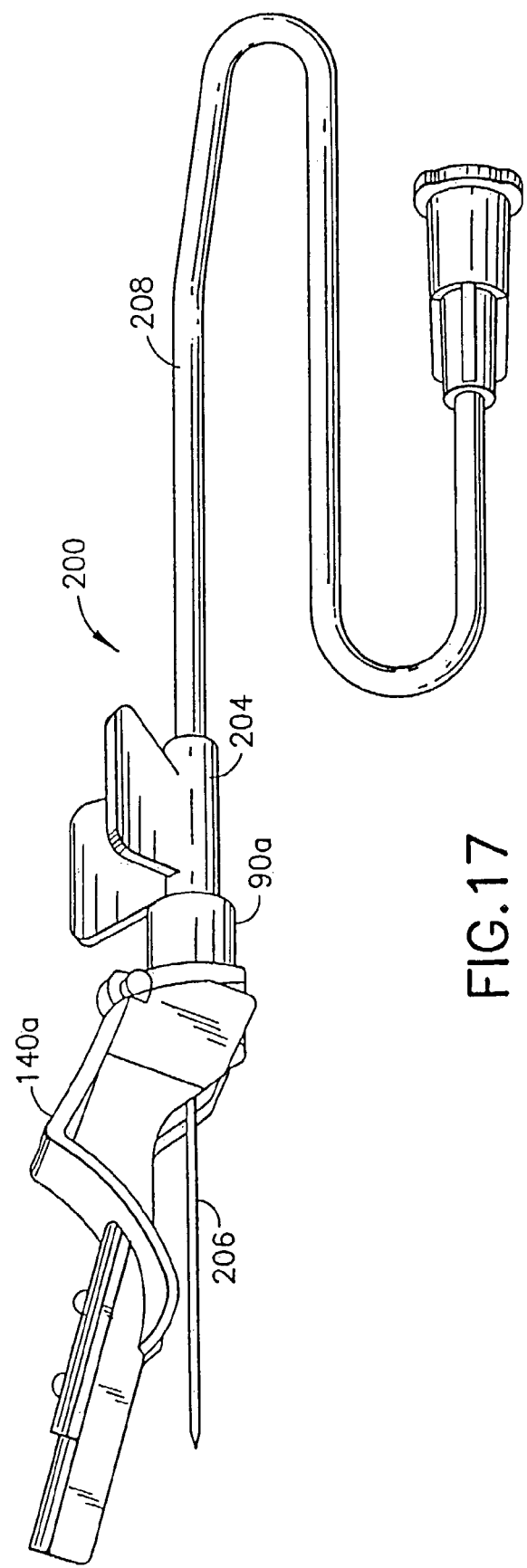
FIG. 17 is a perspective view of an additional embodiment of the present invention in use with a blood collection set.
Figure 18:
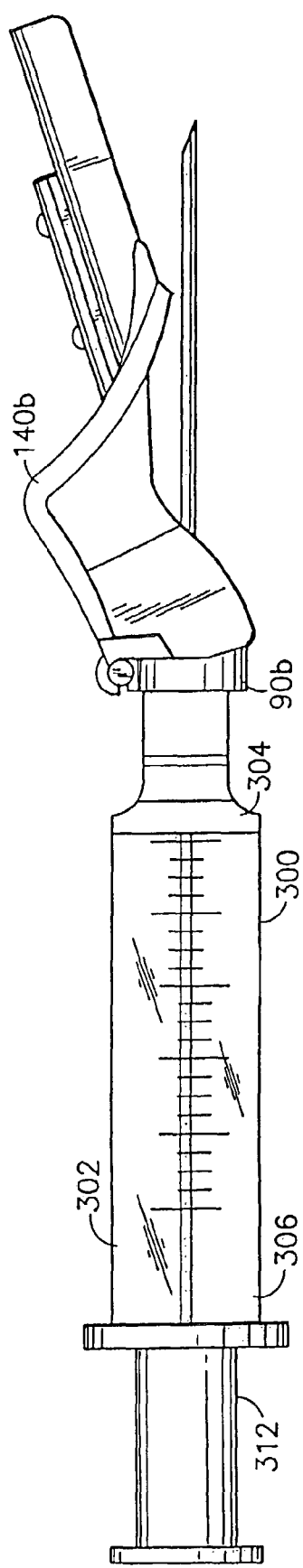
FIG. 18 is a perspective view of an additional embodiment of the present invention in use with a syringe.
Figure 19:
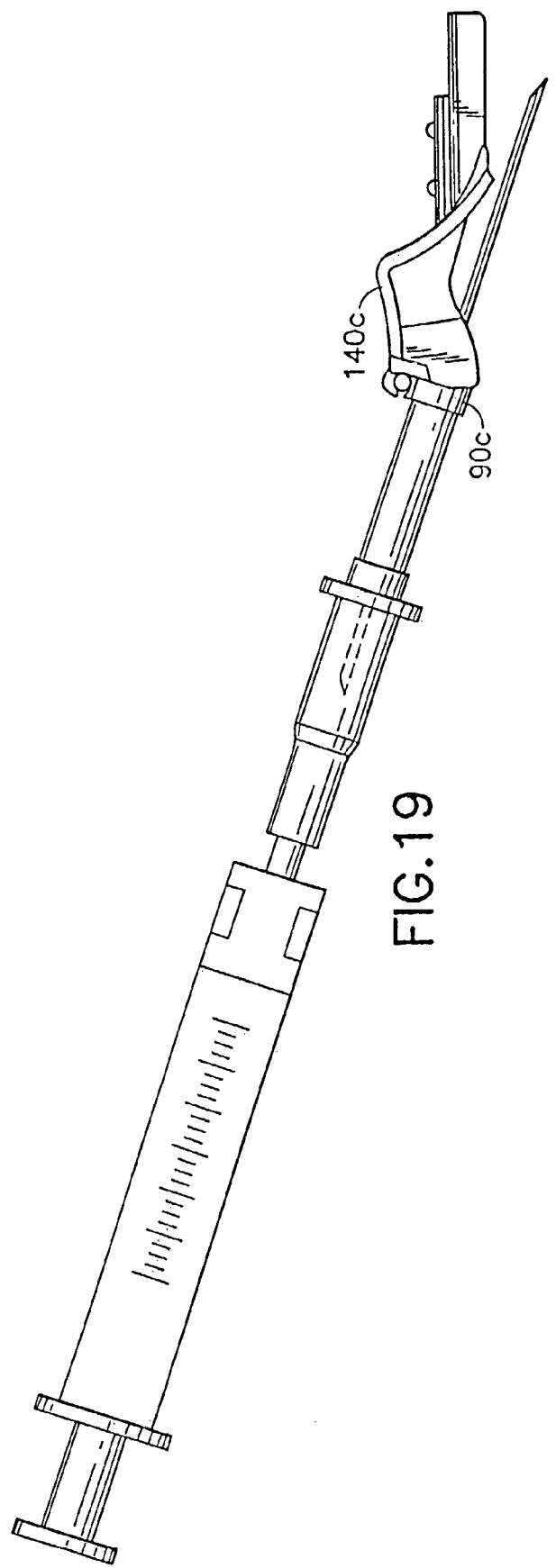
FIG. 19 is a perspective view of an additional embodiment of the present invention in use with a catheter.

FIGS. 17, 18, and 19 are further embodiments of the invention that include may components which are substantially identical to the components of FIGS. 1-3. Accordingly, similar components performing similar functions will be numbered identically to those components of FIGS. 1-3, except that a suffix "a" will be used to identify those similar components in FIG. 17, a suffix "b" will be used to identify those similar components in FIG. 18 and a suffix "c" will be used to identify those similar components in FIG. 19.

Alternatively, the safety shield assembly of the present invention may be used in conjunction with a conventional intravenous (IV) infusion set, as illustrated in FIG. 17.

For purposes of illustration, shield 140a and collar 90a are connected to a conventional IV infusion set, 200, or butterfly structure comprising a needle body with a needle hub 204 extending from the forward end of the needle body and a needle 206 embedded in hub 204. Extending from the rearward end of the needle body is flexible tubing 208 which is conventional and utilized to allow the user to manipulate the structure and to connect it subsequently to supplies of infusion liquids or for the return of collected blood if the arrangement is being used to collect blood.

Infusion set 200 further comprises flexible wings 210 attached to and projecting outwardly from needle hub 204.

Alternatively, the safety shield assembly of the present invention may be used in conjunction with a syringe, as illustrated in FIG. 18.

For purposes of illustration, shield 140b and collar 90b are connected to a conventional hypodermic syringe 300 comprising a syringe barrel 302 having a distal end 304 a proximal end 306 and a plunger 312.

Alternatively, the present invention may be used in conjunction with a catheter as illustrated in FIG. 19.

FIGS. 20 and 21 show a further alternate to the needle assemblies described and illustrated above. In particular, the embodiment of FIGS. 20 and 21 includes a shield 140d that is similar to the shield 140 described and illustrated above. Shield 140d includes a collar engaging area 166d with a top finger guide area 172d and sidewalls 174d that extend downwardly from top finger guide area 172d. Sidewalls 174d differ from the embodiments described and illustrated above in that they extend a shorter distance from top finger guide area 172d and have no means for engaging the chevron-shaped projection on the collar.

Shield 140d includes a forward end 146d with a top wall 163d and sidewalls 162d extending down from top wall 163d. Top wall 163d is characterized by spaced apart mounting apertures 164d.

Shield 140d further includes a channel-shaped clip 220d having a proximal end 222d, a distal end 224d and a top wall 226d extending from distal end 224d toward proximal end 222d. The top wall includes a pair of spaced apart mounting projections 228d that are dimensioned to be mounted in mounting apertures 158d on forward end 146d of shield 140d. Cannula finger locks 230d extend from the channel-shaped clip in a direction away from mounting projections 228d. Each cannula finger lock 230d includes a support leg and a cannula engaging leg 234d. Cannula finger locks 230d are dimensioned and configured to trap the needle cannula when shield 140d is rotated into the closed position.

Proximal end 222d of clip 220d includes a pair of collar engaging legs 236d extending generally proximally from top wall 226d. Cannula engaging legs 236d are configured to pass around opposite respective sides of the collar. Ends of collar engaging legs 236d furthest from top wall 226d are formed with rounded ears 238d. Ears 238d are configured to snap into engagement with the chevron-shaped projection, as described above.

Shield 140d is used substantially exactly as shield 140 described above. In particular, shield 140d can be rotated from the open position to the closed position. As shield 140d approaches the closed position, cannula engaging legs 234d of cannula locking fingers locks 230d engage the needle cannula. Simultaneously, rounded ears 238d engage the chevron-shaped projection. The rounded configuration of ears 238d helps to propel shield 140d toward the closed position. In the closed position, cannula finger locks 230d will snap past the needle cannula for permanently trapping the needle cannula within shield 140d.

The shield and collar of the safety shield assembly of the present invention are comprised of moldable parts which can be mass produced from a variety of materials including, for example, polyethylene, polyvinyl chloride, polystyrene or polyethylene and the like. Materials will be selected which will provide the proper covering and support for the structure of the invention in its use, but which will provide also a degree of resiliency for the purpose of providing the cooperative movement relative to the shield and the collar of the assembly.

Figure 22:
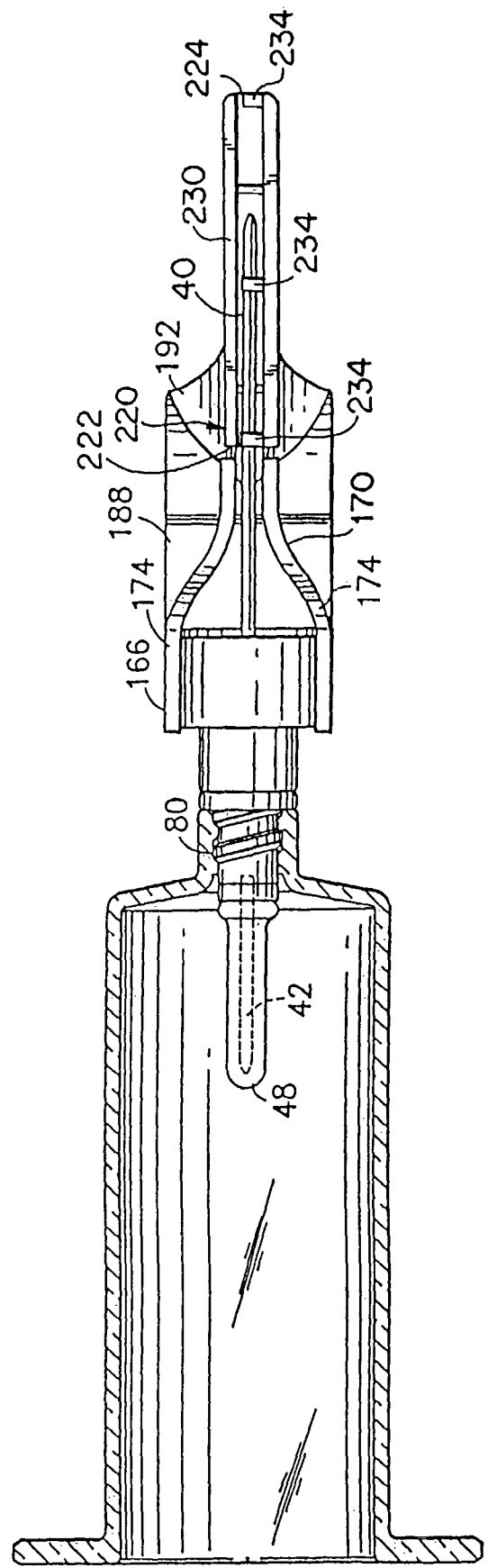
FIG. 22 is a bottom view of the assembly similar to FIG. 15A, but showing an additional embodiment of the present invention without a chevron-shaped structure on the collar and without locking ears on the shield.

A further alternate embodiment is illustrated in FIG. 22, and is virtually identical to the embodiment of the invention depicted in FIG. 15A. As a result, comparable numerals have been employed to identify identical or very similar components. FIG. 22, however, differs from FIG. 15A in that collar 90 does not have the chevron-shaped protrusion 118 illustrated in FIG. 15A. Additionally, shield 140 does not have ears comparable to rounded ears 194 of FIG. 15A. Thus, the embodiment illustrated in FIG. 22 relies entirely upon the engagement of cannula finger locks 234 with needle 40. There are fewer structures on the embodiment of FIG. 22 to achieve the clear audible and tactile indication of complete shielding as in the previous embodiment and no structure for accelerating shield 140 in to the second position around needle 40. However, upon complete shielding, the retention between shield 140 and needle 40 in the embodiment of FIG. 22 is comparable to the retention achieved by the previous embodiments.

What is claimed is:

1. A safety needle assembly comprising
a needle hub with proximal and distal ends and a passage extending between said ends,
a needle cannula mounted to said passage of said needle hub and having a pointed distal end projecting beyond said distal end of said hub,
a shield having proximal and distal ends, said proximal end of said shield being hingedly mounted to said hub for rotation from a first position where said shield is spaced from said needle cannula to a second position where said shield substantially shields said needle cannula, said shield comprising at least one support wall, and a channel mounted to said support wall, said channel having a top wall and opposed first and second sidewalls extending from said top wall, and at least one resiliently deflectable cannula finger lock projecting from said first sidewall angularly toward said top wall, wherein said channel can be selectively mounted to said support wall in one of a plurality of orientations in relation to one another.

2. The safety needle assembly of claim 1, further comprising a medical device connected to said needle hub.

3. The safety needle assembly of claim 2, wherein the medical device comprises a holder for releasably receiving a fluid collection tube.

4. The safety needle assembly of claim 2, wherein the medical device is a syringe.

5. The safety needle assembly of claim 2, wherein the medical device comprises an intravenous infusion set.

6. The safety needle assembly of claim 1, wherein said needle cannula includes a proximal end, said needle cannula extending entirely through said passage of said hub such that said proximal end of said needle cannula projects proximally beyond said proximal end of said hub.

7. The safety needle assembly of claim 6, further comprising an elastomeric sleeve mounted over said proximal end of said needle cannula and securely engaged to said proximal end of said hub.

8. The safety shield assembly of claim 1, wherein said needle hub comprises an inner tubular portion securely mounted to said needle cannula and an outer collar securely mounted over said inner tubular portion, said shield being hingedly mounted to said collar of said hub.

9. The safety needle assembly of claim 1, wherein said support wall comprises a plurality of apertures extending therethrough, said channel having a plurality of mounting projections formed thereon, said mounting projections being dimensioned and disposed for locked engagement with said apertures in said support wall.

10. The safety needle assembly of claim 1, wherein portions of said shield adjacent said proximal end are configured for partly surrounding said hub, said support wall extending substantially rigidly from said portions of said shield dimensioned for partly surrounding said hub.

11. The safety needle assembly of claim 1, wherein said channel has an elongate convexly arcuate outer surface, said support wall having a concave surface for closely receiving said convex outer surface of said channel.

12. The safety needle assembly of claim 1, wherein said at least one cannula finger lock comprises a plurality of cannula finger locks.

13. A safety needle assembly comprising
a needle hub with proximal and distal ends and a passage extending between said ends,
a needle cannula mounted to said passage of said needle hub and having a pointed distal end projecting beyond said distal end of said hub,
a shield having proximal and distal ends, said proximal end of said shield being hingedly mounted to said hub for rotation from a first position where said shield is spaced from said needle cannula to a second position where said shield substantially shields said needle cannula, said shield comprising at least one support wall, and a channel mounted to said support wall, said channel having a top wall and opposed first and second sidewalls extending from said top wall, and at least one resiliently deflectable cannula finger lock, wherein said top wall of said channel comprises mounting structure for mounting said channel to said support wall, whereby said channel can be disposed in either a first orientation or in a second orientation relative to said support wall for altering positions of said channel relative to said needle cannula.

14. The safety needle assembly of claim 13, wherein said support wall has a distal end remote from said proximal end of said shield, said channel being dimensioned such that, in said second orientation of said channel relative to said support wall, said second end of said channel projects distally beyond said distal end of said support wall.

15. The safety needle assembly of claim 14, wherein said channel is dimensioned such that in said first orientation, said first end of said channel substantially aligns with said distal end of said support wall.

16. The needle assembly of claim 15, wherein said channel is dimensioned such that in said first orientation, said second end of said channel is substantially adjacent said proximal end of said shield.

17. The safety needle assembly of claim 13, wherein said at least one cannula finger lock comprises a plurality of cannula finger locks, a first of said cannula finger locks being substantially adjacent said first end of said channel and a second of said cannula finger locks being substantially adjacent said second end of said channel.

18. The safety needle assembly of claim 13, wherein said channel further comprising first and second longitudinal ends, said mounting structure being closer to said first end of said channel than to said second end.

19. A safety needle assembly comprising
a needle hub with proximal and distal ends and a passage extending between said ends,
a needle cannula mounted to said passage of said needle hub and having a pointed distal end projecting beyond said distal end of said hub,
a shield having proximal and distal ends, said proximal end of said shield being hingedly mounted to said hub for rotation from a first position where said shield is spaced from said needle cannula to a second position where said shield substantially shields said needle cannula, said shield comprising at least one support wall, a channel mounted to said support wall, said channel having a top wall and opposed first and second sidewalls extending from said top wall, at least one cannula finger lock projecting from said first sidewall angularly toward said top wall,
wherein said support wall comprises at least one aperture extending therethrough, said channel having at least one mounting projection formed thereon, said at least one mounting projection being dimensioned and disposed for locked engagement with said at least one aperture in said support wall.

20. The safety needle assembly of claim 19, wherein said support wall comprises a plurality of apertures extending therethrough, said channel having a plurality of mounting projections formed thereon, said mounting projections being dimensioned and disposed for locked engagement with said apertures in said support wall.

21. The safety needle assembly of claim 19, wherein portions of said shield adjacent said proximal end are configured for partly surrounding said hub, said support wall extending substantially rigidly from said portions of said shield dimensioned for partly surrounding said hub.

22. The safety needle assembly of claim 19, wherein said channel has an elongate convexly arcuate outer surface, said support wall having a concave surface for closely receiving said convex outer surface of said channel.

* * * * *